(12) United States Patent
Watkins et al.

(10) Patent No.: US 9,757,504 B2
(45) Date of Patent: Sep. 12, 2017

(54) SYSTEMS AND METHODS FOR PERFORMING HEMODIALYSIS

(71) Applicants: BAXTER INTERNATIONAL INC., Deerfield, IL (US); BAXTER HEALTHCARE SA, Glattpark (Opfikon) (CH)

(72) Inventors: Randolph H. Watkins, Wonder Lake, IL (US); Steven J. Wurgler, San Antonio, TX (US); Shincy Maliekkal, Glenview, IL (US); Sujatha Karoor, Lake Forest, IL (US); Katrina Smith, Fox Lake, IL (US)

(73) Assignees: BAXTER INTERNATIONAL INC., Deerfield, IL (US); BAXTER HEALTHCARE SA, Glattpark (Opfikon) (CH)

( * ) Notice: Subject to any disclaimer, the term of this patent is extended or adjusted under 35 U.S.C. 154(b) by 155 days.

(21) Appl. No.: 14/594,306

(22) Filed: Jan. 12, 2015

(65) Prior Publication Data

US 2015/0122714 A1 May 7, 2015

Related U.S. Application Data

(62) Division of application No. 12/338,052, filed on Dec. 18, 2008, now Pat. No. 8,961,789.

(Continued)

(51) Int. Cl.
*A61M 1/16* (2006.01)
*B01D 63/16* (2006.01)
(Continued)

(52) U.S. Cl.
CPC ............ *A61M 1/1623* (2014.02); *A61M 1/26* (2013.01); *A61M 1/265* (2014.02);
(Continued)

(58) Field of Classification Search
None
See application file for complete search history.

(56) References Cited

U.S. PATENT DOCUMENTS 1,664,769 A 4/1928 Chance
2,197,509 A 4/1940 Morton
(Continued)

FOREIGN PATENT DOCUMENTS

DE 1442874 A1 11/1968
DE 3043682 A1 7/1981
(Continued)

OTHER PUBLICATIONS

Bhagat et al., Filtration Studies with Ultrafine Particles, Sep. 1966. University of California, Lawrence Radiation Laboratory, Berkeley, CA, UCRL-16574, preprint release for announcement in Nuclear Science Abstracts.

(Continued)

*Primary Examiner* — Dirk Bass
(74) *Attorney, Agent, or Firm* — Marshall, Gerstein & Borun LLP

(57) ABSTRACT

Systems and methods for performing hemodialysis to remove metabolic waste from the blood of a patient are disclosed. The systems and methods preferably comprise at least one blood processing apparatus that receives whole blood from a patient. Cellular blood components are removed from the whole blood by hemofiltration, to provide filtered plasma comprising metabolic waste that is substantially reduced of blood cells. The cellular blood components may be returned to the patient. The filtered plasma comprising waste may be removed from the blood processing apparatus through a waste path for further processing in a separate apparatus, or in the same apparatus in a second stage processing procedure to remove metabolic waste components and excess water from the plasma by hemodialysis.

(Continued)

At least one of the hemofiltration and hemodialysis processing apparatus comprises a Taylor vortex-enhanced separation apparatus.

9 Claims, 5 Drawing Sheets

Related U.S. Application Data

(60) Provisional application No. 61/110,427, filed on Oct. 31, 2008.

(51) Int. Cl.
*A61M 1/26* (2006.01)
*A61M 1/34* (2006.01)
*B01D 65/08* (2006.01)

(52) U.S. Cl.
CPC ........ *A61M 1/3472* (2013.01); *A61M 1/3479* (2014.02); *B01D 63/16* (2013.01); *B01D 65/08* (2013.01); *B01D 2315/02* (2013.01); *B01D 2321/2033* (2013.01)

(56) References Cited

U.S. PATENT DOCUMENTS

| | | |
|---|---|---|
| 2,294,248 A | 8/1942 | Smulski |
| 2,398,233 A | 4/1946 | Lincoln |
| 2,670,849 A | 3/1954 | Dunmire |
| 2,709,500 A | 5/1955 | Carter |
| 3,026,871 A | 3/1962 | Thomas |
| 3,183,908 A | 5/1965 | Collins |
| 3,355,382 A | 11/1967 | Huntington |
| 3,396,103 A | 8/1968 | Huntington |
| 3,400,074 A | 9/1968 | Grenci |
| 3,491,887 A | 1/1970 | Maestrelli |
| 3,523,568 A | 8/1970 | Van Leeuwen |
| 3,567,030 A | 3/1971 | Loeffler et al. |
| 3,568,835 A | 3/1971 | Hansen |
| 3,634,228 A | 1/1972 | Latham |
| 3,647,632 A | 3/1972 | Himmelfarb |
| 3,674,440 A | 7/1972 | Kitrilakis |
| 3,705,100 A | 12/1972 | Agranat et al. |
| 3,750,885 A | 8/1973 | Fournier |
| 3,771,658 A | 11/1973 | Brumfield |
| 3,771,899 A | 11/1973 | Brumfield |
| 3,795,318 A | 3/1974 | Crane et al. |
| 3,821,108 A | 6/1974 | Manjikian |
| 3,830,372 A | 8/1974 | Manjikian |
| 3,847,817 A | 11/1974 | Jarman |
| 3,883,434 A | 5/1975 | Gayler |
| 3,900,290 A | 8/1975 | Hornstra |
| 3,900,398 A | 8/1975 | Gillette |
| 3,946,731 A | 3/1976 | Lichtenstein |
| 3,977,976 A | 8/1976 | Spaan et al. |
| 4,040,965 A | 8/1977 | Kohlheb |
| 4,062,771 A | 12/1977 | Saupe |
| 4,066,554 A | 1/1978 | Guyer |
| 4,082,668 A | 4/1978 | Zeineh et al. |
| 4,093,552 A | 6/1978 | Guyer |
| 4,113,614 A | 9/1978 | Rollo et al. |
| 4,184,952 A | 1/1980 | Stewart |
| 4,191,182 A | 3/1980 | Popovich et al. |
| 4,212,741 A | 7/1980 | Brumfield |
| 4,212,742 A | 7/1980 | Solomon et al. |
| 4,214,990 A | 7/1980 | Joh |
| 4,229,291 A | 10/1980 | Walch et al. |
| 4,303,068 A | 12/1981 | Zelman |
| 4,381,999 A | 5/1983 | Boucher et al. |
| 4,412,553 A | 11/1983 | Kopp et al. |
| 4,444,596 A | 4/1984 | Gortz et al. |
| 4,486,303 A | 12/1984 | Brous |
| 4,490,135 A | 12/1984 | Troutner |
| 4,493,693 A | 1/1985 | Bilstad et al. |
| 4,535,062 A | 8/1985 | Muller |
| 4,579,662 A | 4/1986 | Jonsson |
| 4,753,729 A | 6/1988 | Schoendorfer et al. |
| 4,776,964 A | 10/1988 | Schoendorfer et al. |
| 4,790,942 A | 12/1988 | Shmidt et al. |
| 4,871,462 A | 10/1989 | Fischel et al. |
| 4,876,013 A | 10/1989 | Shmidt et al. |
| 4,919,817 A | 4/1990 | Schoendorfer et al. |
| 4,965,846 A | 10/1990 | Williamson, IV |
| 5,000,848 A | 3/1991 | Hodgins et al. |
| 5,034,135 A | 7/1991 | Fischel |
| 5,135,667 A | 8/1992 | Schoendorfer |
| 5,194,145 A | 3/1993 | Schoendorfer |
| 5,370,802 A | 12/1994 | Brown |
| 5,376,263 A | 12/1994 | Fischel |
| 5,464,534 A | 11/1995 | Fischel |
| 5,738,792 A | 4/1998 | Schoendorfer |
| 5,783,085 A | 7/1998 | Fischel |
| 5,865,785 A | 2/1999 | Bischof |
| 5,919,369 A | 7/1999 | Ash |
| 6,099,730 A | 8/2000 | Ameer et al. |
| 6,730,054 B2 | 5/2004 | Pierce et al. |
| 6,852,231 B2 | 2/2005 | Ivansons et al. |
| 6,863,821 B2 | 3/2005 | Moriarty et al. |
| 7,182,867 B2 | 2/2007 | Moriarty et al. |
| 7,220,354 B2 | 5/2007 | McLaughlin et al. |
| 7,374,677 B2 | 5/2008 | McLaughlin et al. |
| 2003/0146154 A1 | 8/2003 | Moriarty et al. |
| 2003/0155312 A1 | 8/2003 | Ivansons et al. |
| 2004/0238445 A1 | 12/2004 | McLaughlin et al. |
| 2006/0041216 A1 | 2/2006 | McLaughlin et al. |
| 2006/0278581 A1 | 12/2006 | Moriarty et al. |
| 2007/0181500 A1 | 8/2007 | Moriarty et al. |
| 2008/0195025 A1 | 8/2008 | McLaughlin et al. |
| 2008/0197076 A1 | 8/2008 | McLaughlin et al. |

FOREIGN PATENT DOCUMENTS

| | | |
|---|---|---|
| EP | 0052004 A1 | 5/1982 |
| EP | 0076665 A2 | 4/1983 |
| EP | 0112152 A2 | 6/1984 |
| FR | 1583221 A | 10/1969 |
| GB | 1283273 A | 7/1972 |
| GB | 1480406 A | 7/1977 |
| RU | 197801 | 11/1963 |
| SE | 77114254 | 10/1977 |
| WO | WO-81/02979 A1 | 10/1981 |
| WO | WO-82/03567 A1 | 10/1982 |
| WO | WO-82/03568 A1 | 10/1982 |
| WO | WO-85/02783 A1 | 7/1985 |
| WO | WO-85/04112 A1 | 9/1985 |

OTHER PUBLICATIONS

Castino, The Filtration of Plasma From Whole Blood: A Novel Approach to Clinical Detoxification, Publication #395 from the Blood Research Laboratory, The American National Red Cross, undated.

Colton, Fundamentals of Gas Transport in Blood, reprinted from Artificial Lungs for Acute Respiratory Failure. Theory and Practics, W.M. Zapol and J. Qvist, Eds., Academic Press, N.Y. (1976).

Eckstein et al.: Self-Diffusion of Particles in Shear Flow of a Suspension, J. Fluid Mech. 1977, vol. 79, part 1, pp. 191-208.

Forstrom et al.: Formed Element Deposition Onto Filtering Walls, vol. XXI Trans. Amer. Soc. Artif. Int. Organs, pp. 602-607, 1975.

Gaylor et al.: Gas Transfer and Thrombogenesis in an Annular Membrane Oxygenator With Active Blood Mixing, vol. XIX Trans. Amer. Soc. Artif. Int. Organs, 1973.

Hallstrom et al.: Descriptions of a Rotating Ultra-filtration Module, Department of Food Engineering, Lund University (Sweden), Desalination vol. 24, pp. 273-279, (1978).

Kitrilakis et al.: A Rotating Disk Membrane Oxygenator, 1976 Hemisphere Publishing Corporation, Washington—London, pp. 211-221.

Kozinski, Protein Ultrafiltration: A General Example of Boundary Layer Filtration, A1ChE Journal, vol. 18, No. 5, Sep. 1972.

(56) References Cited

OTHER PUBLICATIONS

Lieberherr, Hydrodynamic of Annular Gap Flo Between Permeable Cylinder Walls, 532.54: 66.067.17, Escher Wyss Mitteilungen Feb. 1978-Jan. 1979.
Lopez-Leiva, Ultrafiltration at Low Degrees of Concentration: Technical Possibilities, Desalination, vol. 35, pp. 115-128, 1980.
Lopez-Leiva, Ultrafiltration in Rotary Annular Flow, undated.
Margaritis et al., Engineering Analysis of the Rotorfermentor, Department of Chemical Engineering and Lawrence Berkeley Laboratory, University of California 94720, undated.
Robinson, How Does Fluid Flow Become Turbulent, Science, vol. 221, pp. 140-143, Jul. 1983.
Schindhelm et al., Mass Transfer Characteristics of Plasma Filtration Membranes, Trans. Am. Soc. Artificial Organs, vol. XXVII, pp. 554-558, 1981.
Schlichting et al., Boundary-Layer Theory, 6th Ed. McGraw-Hill Series in Mechanical Engineering, pp. 500-505, 1968.
Sherwood, Desalination by Reverse Osmosis, I & EC Fundamentals, vol. 6 (1) pp. 2-12, Feb. 1967.
Solomon, Membrane Separations: Technological Principles and Issues, Trans. Am. Soc. Artif. Int. Organs, pp. 345-350, 1981.
Solomon, Continuous Flow Membrane Filtration of Plasma from Whole Blood, vol. XXIV Trans. Am. Soc. Artif. Int. Organs, pp. 23-26, 1978.
Strong, An Experimental Study of Mass Transfer in Rotating Couette Flow with Low Axial Reynolds Number, The Canadian Journal of Chemical Engineering, vol. 54, pp. 295-298, Aug. 1976.
Taylor, Distribution of Velocity & Temperature Between Concentric Rotating Cylinders, Taylor, Proc. Roy. Soc., A, vol. 135, pp. 494-512, 1932.
Taylor, Stability of a Viscous Liquid Contained Between Rotating Cylinders, Phil Trans Roy. Soc., A223:289, Feb. 8, 1923.
Tobler, Dynamic Filtration: The Engineering Concept of the Escher Wyss Pressure Filter, Filtration & Separation, Jul./Aug. 1982.
Werynski, Membrane Plasma Separation: Toward Improved Clnical Operation, Trans. Am Soc. Artificial Organs, vol. XXVII, pp. 554-558, 1981.
Wiltbank et al., Filtration Plasmapheresis in Vivo, Transfusion, vol. 21, No. 5, pp. 502-510, undated.
Wood, A Thesis: Deposition of Red Blood Cells Onto Filtering Surfaces, submitted to the Graduate School of the University of Minnesota in partial fulfillment of requirements for M.S. degree in mechanical engineering, Degree granted 1974.
Zydney et al., Continuous Flow Membrane Plasmapheresis: Theoretical Models for Flux and Hemolysis Prediction, Trans Am Soc Artif Intern Organs, vol. XXVIII, pp. 408-411, 1982.

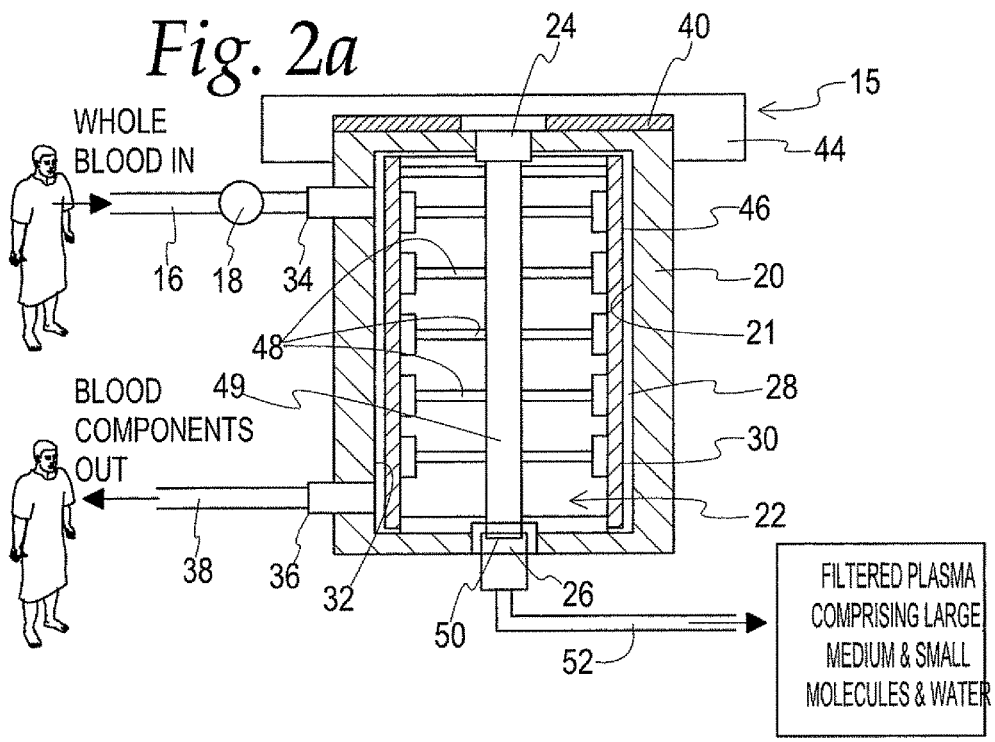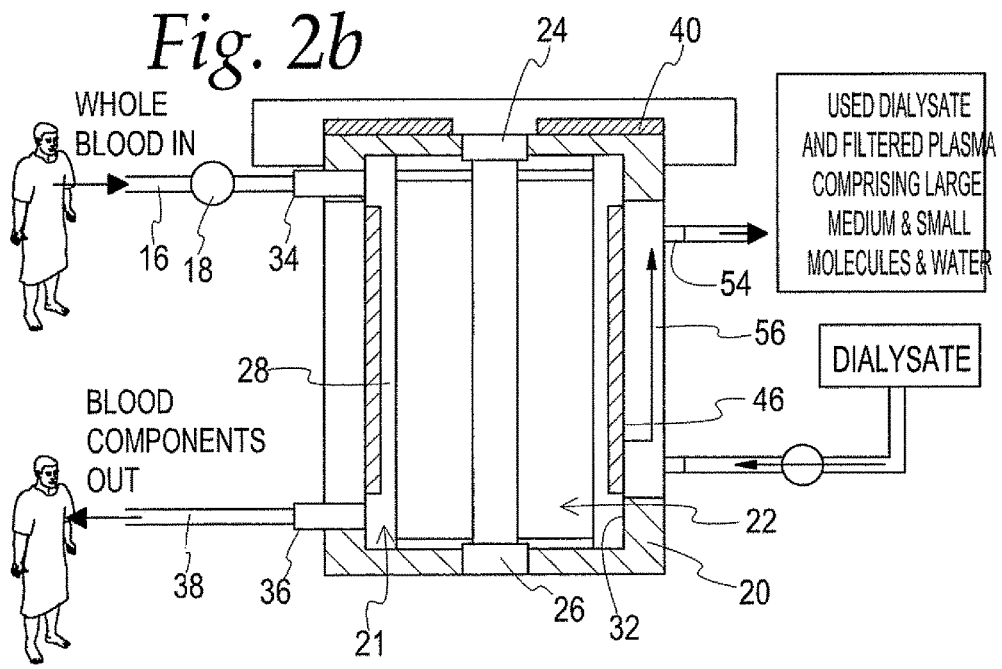

*Fig. 5*
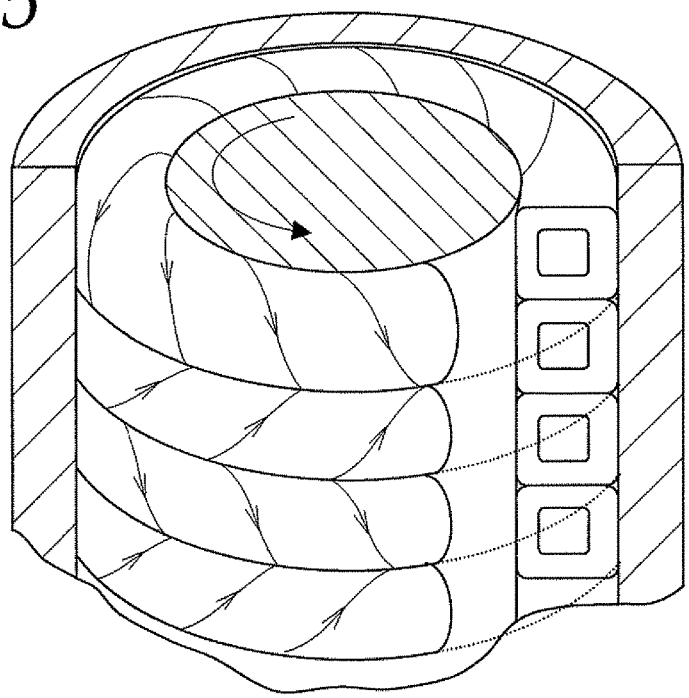
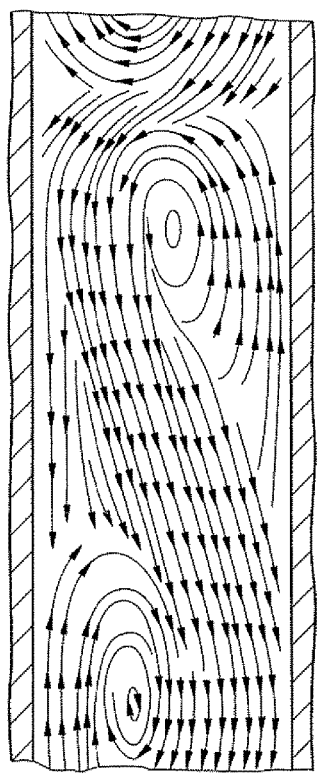
*Fig. 6*

SYSTEMS AND METHODS FOR PERFORMING HEMODIALYSIS

RELATED APPLICATIONS

This is a divisional of and claims the priority benefit of U.S. application Ser. No. 12/338,052, filed Dec. 18, 2008, which itself claims the priority benefit of U.S. Provisional Application Ser. No. 61/110,427, filed Oct. 31, 2008. The entire contents of each of the foregoing is incorporated herein by reference.

FIELD OF THE INVENTION

The subject matter of the present application relates generally to systems and methods for performing hemodialysis.

BACKGROUND

For various reasons, including end-stage renal disease or E.S.R.D., illness, injury or surgery, patients may require replacement or supplementation of their natural renal function in order to remove excess fluid and/or metabolic waste products from their blood. Hemodialysis employing hollow fiber membranes, and peritoneal dialysis are among the most common dialysis techniques. More recently, the use of devices employing the passage of blood between two relatively moving surfaces, and more particularly, between two relatively rotating surfaces which can create Couette flow and so-called Taylor vortices has been proposed for dialysis. Examples of such devices and systems are described in U.S. Pat. Nos. 6,863,821 and 7,182,867 to Moriarty et al., and U.S. Publications Nos. 2006-0278581 (Ser. No. 11/465,952) and 2007-0181500 (Ser. No. 11/734,579), also to Moriarty et al, which are incorporated herein by reference.

Further examples of such devices and systems for dialysis may be found in U.S. Patent Application Publications 2004-0238445, 2006-0041216 and 2007-0193941 to McLaughlin et al., also incorporated by reference herein. Application No. 2006-0041216 specifically describes employing such a device in a two-stage dialysis procedure in which at least one of the stages employs a Taylor-vortex enhanced blood filtration device. However, the system described in that application is largely directed at avoiding the need for large volumes of new replacement fluid by generating replacement fluid from the fluid removed from the patient. It also discloses recycling dialysate employed in the dialysis. The disclosed process and system, however, are potentially substantially slower than other dialysis systems, adding to the burden of lengthy procedure times already experienced by most hemodialysis patients.

SUMMARY

In accordance with one aspect of the subject matter of the application, a method for performing hemodialysis on a patient to remove metabolic waste from the patient's blood is provided. The method preferably comprises conveying the blood of a patient through a first gap defined between a first inner surface and a first outer surface, wherein at least one of the first inner and outer surfaces is carrying a filter membrane. The first inner and outer surfaces are moved relative to each other, which may create fluid shear forces, such as by Couette flow and, more specifically, Taylor vortices along the first inner and outer surfaces. Plasma comprising metabolic waste components is passed through the membrane, while passage of blood cells through the membrane is substantially prevented, thereby yielding filtered plasma (and metabolic waste) substantially reduced of blood cells.

The filtered plasma is conveyed through a second gap defined between a second inner surface and a second outer surface. At least one of the second inner and outer surfaces is carrying a diffusion membrane such as a hemodialysis membrane. The second inner and outer surfaces are moved relative to each other, which may create fluid shear forces, such as by Couette flow and, more specifically, Taylor vortices along the second inner and outer surfaces. Fresh dialysis solution may be conveyed along an opposite side of the hemodialysis membrane to create a concentration gradient across the hemodialysis membrane to transport waste components, such as by diffusion, from the plasma through the diffusion membrane to provide plasma that is substantially reduced of waste components.

In accordance with another aspect of the subject matter of the application, a blood processing system for performing hemodialysis on a patient to remove metabolic waste from the patient's blood is provided. The system preferably comprises a blood processing apparatus and a flow path for fluid communication between a patient and the blood processing apparatus. The blood processing apparatus comprises spaced apart first inner and first outer surfaces defining a first gap therebetween. At least one of the first inner and first outer surfaces of the apparatus carries a filter membrane. A flow path communicates with the first gap for flowing blood therethrough.

The blood processing apparatus further comprises a drive assembly for causing relative movement between the first inner and first outer surfaces to create movement of the patient's blood within the first gap to induce transport of plasma comprising waste through the membrane. The relative movement between the first inner and outer surfaces may create fluid shear forces, such as by Couette flow and, more specifically, Taylor vortices within the first gap. Passage of blood cells through the membrane is substantially prevented to provide filtered plasma comprising waste that is substantially reduced of blood cells.

The blood processing apparatus further preferably comprises a second inner surface and a second outer surface spaced apart to define a second gap, wherein at least one of the second inner and second outer surfaces carries a diffusion membrane, such as a hemodialysis membrane. A drive assembly (which may be the same drive assembly first mentioned) causes relative movement between the second inner and outer surfaces. The relative movement between the second inner and outer surfaces may create fluid shear forces, such as by Couette flow and, more specifically, Taylor vortices, between the second inner and outer surfaces to create movement of plasma comprising waste within the second gap that induces transport of waste through the hemodialysis membrane. The blood processing apparatus may further comprise a channel to convey fresh dialysis solution along the side of a hemodialysis membrane facing away from the second gap to create a concentration gradient across the hemodialysis membrane to induce transport of waste through the membrane.

Various other features and advantages of the subject matter of the present application are set forth in the following description and drawings, as well as in the appended claims.

BRIEF DESCRIPTION OF THE DRAWINGS

FIG. 2a is a side cross-sectional view of one embodiment of a blood processing apparatus that the system and method shown in FIG. 1 can incorporate for the purpose of separating cellular components of blood from plasma including metabolic waste.

FIG. 2b is a side cross-sectional view of another embodiment of a blood processing apparatus that the system and method shown in FIG. 1 can incorporate for the purpose of separating cellular components of blood from plasma including metabolic waste.

FIG. 5 is an enlarged and simplified perspective view of a gap formed between spaced apart inner and outer surfaces of the blood processing apparatus shown in FIG. 2a and other figures that can be rotated relative to each other creating fluid shear forces, such as by Couette flow and, more specifically, Taylor vortices in the fluid flowing through the gap.

FIG. 6 is an enlarged side sectional view of the vortex flow conditions shown in FIG. 5.

DETAILED DESCRIPTION

Figure 1:
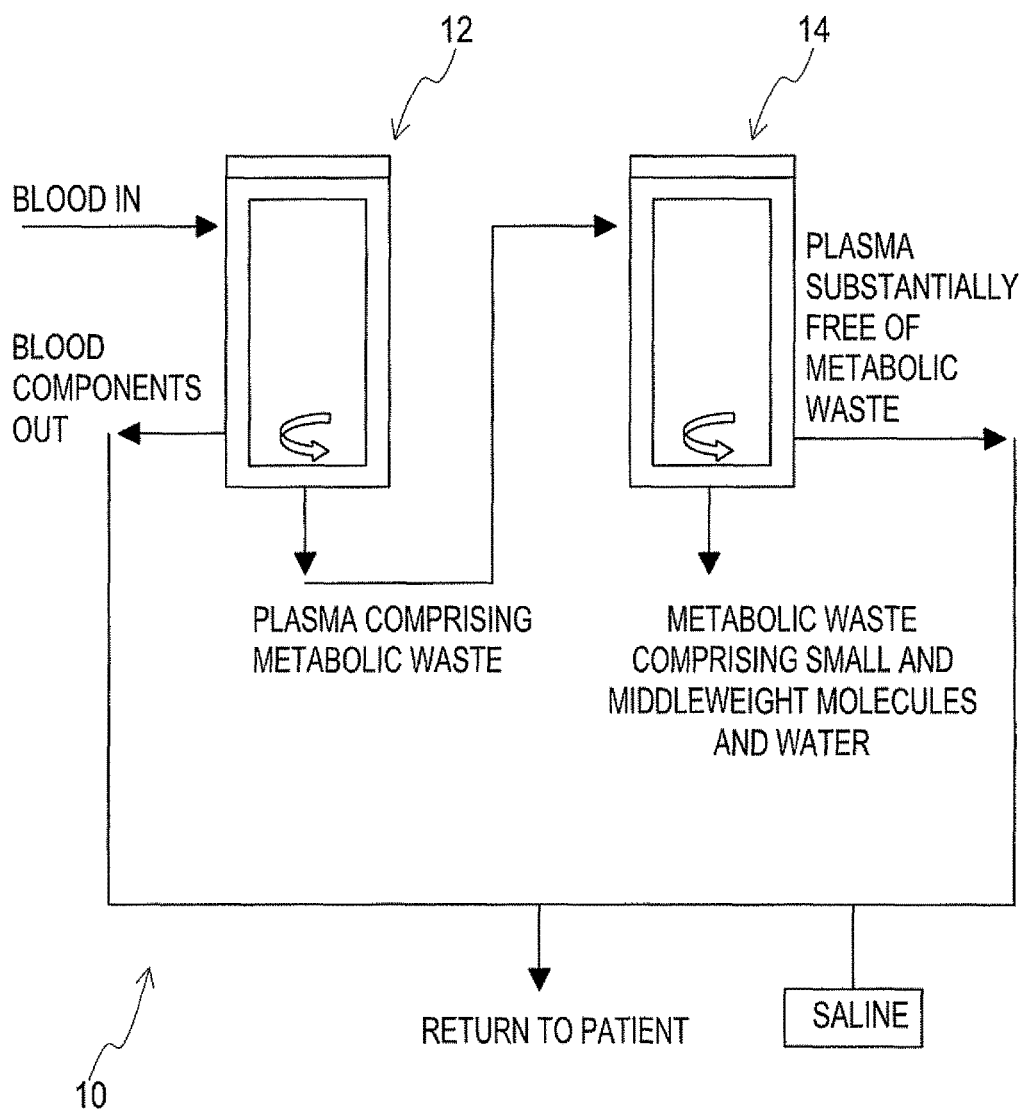
FIG. 1 is a schematic view of a two-stage system and method that includes a blood processing apparatus for performing hemodialysis on a patient to remove metabolic waste from the patient's blood.

FIG. 1 illustrates schematically the system and method described herein for performing hemodialysis on a patient to reduce the levels of metabolic waste in a patient's blood. More specifically, the system illustrated in FIG. 1 depicts a two-stage dialysis system 10 for removing waste material (e.g., urea, creatinine, and uric acid) and excess water from the blood of an individual whose renal function may be impaired or lacking. The system includes a first stage, generally at 12, in which blood cells, such as red cells, platelets and leukocytes, are removed from blood for return to the patient, leaving filtered plasma which has been reduced of blood cells. The filtered plasma may include large molecules and most of the waste products of metabolism particularly including generally middleweight and small-weight molecules and water. The filtered plasma is passed through a second stage, generally at 14, in which metabolic waste comprising small and generally middleweight molecules and water are removed, leaving plasma that is substantially reduced of metabolic waste and water for return to the patient. The first stage removal of cellular components allows the plasma to be processed with increased speed and efficiency in the second stage, with consequent reduced patient treatment time and inconvenience.

Although the process described is carried out in two or more stages, it does not necessarily require two separate devices or apparatus, as will be discussed in more detail hereinafter, and the process may be carried out in a single device that is configured to include multiple stages. Also, although shown as a two stage process, this is for purposes of description only and does not preclude the use of additional stages or processing steps.

FIGS. 2a and 2b illustrate alternative embodiments of a separation apparatus that may be employed in the first stage of the processing system illustrated in FIG. 1. Whole blood, which may be anticoagulated to reduce clotting, is conveyed from an individual patient into the first stage. The individual may have one or more surgically installed vascular access devices, such as arterial-venous shunts, to facilitate coupling of the first stage to the blood circulatory system of the patient. Alternatively, a phlebotomy needle or other suitable means may be used to access the patient's circulatory system.

As noted above, anticoagulant may be added to the whole blood as it is withdrawn from the patient to reduce clotting. The flow rate of the blood may be controlled by a typical pump, such as a peristaltic pump 18 on the blood inlet flow path 16 between the patient and first stage apparatus 15. As shown in FIG. 2a, in the illustrated embodiment, the first stage apparatus 15 includes a generally cylindrical outer housing 20 having a cylindrical internal chamber 21 and containing a cylindrical rotor or spinner 22 rotatably supported within the housing, such as between oppositely spaced pivot bearings at 24 and 26 located at the ends of cylindrical housing.

As shown, the outside diameter of the rotor is smaller than the inside diameter of the cylindrical housing, forming a gap 28 between the outer surface 30 of the rotor and the inner surface 32 of the housing. Whole blood from the inlet path 16 flows through an inlet port 34 in the housing 20 and into the gap 28 between the rotor and housing surfaces. The whole blood flows along the gap 28, where separation of the blood cell components takes place, as will be described in more detail below. The blood components and particularly the cellular components of the blood, including red cells, white cells and platelets, are then removed through outlet port 36 of housing 20 for return to the patient through return flow path 38.

The rotor axis may be coincident with the axis of the housing chamber 21, in which case the width of the gap 28 is uniform annularly around the rotor. Alternatively, the rotor axis may be offset from the axis of the housing chamber so that the width of the gap annularly varies around the surface of the rotor.

In the embodiment illustrated in FIG. 2a and other figures, for example, the rotor 22 is rotated by a drive system of the type which preferably rotates the rotor without requiring openings or mechanical access through the housing 20. As an example, in one embodiment, a ring such as a star or lobe-shaped ring, of magnetic material 40 is fixed to or otherwise cooperative with the rotor 22. The ring of magnetic material is acted upon by an external rotating magnetic field generated by an external rotating magnetic drive member or system 44. The magnetic drive system may be associated with a durable or reusable hardware system for cooperation with the separation apparatus 15 and an associated flow circuit, which may be disposable and intended for one-time use only and to be discarded after use.

The external drive system 44 causes rotation of the rotor 22 relative to the stationary interior wall of the housing, rotating the rotor at a pre-selected velocity which may be selected by the operator or by an automated control system depending on the particular processing procedure being carried out, the dimension of the gap 28 and the flow rates of the blood components flowing through the system. The movement of one surface relative to another creates turbulence in the blood passing through the gap 28, creating high levels of shear forces along the gap surfaces, such as by Couette flow and, more specifically, as illustrated in FIGS. 6 and 7, the rotation of the rotor relative to the stationary interior wall creates Taylor vortices along the gap surfaces, which tends to clear the gap surfaces and enhance separation efficiencies. More details of the system illustrated in FIG. 2a and other figures and the associated drive system are found in U.S. Pat. No. 5,194,145, which is hereby incorporated by reference.

In the illustrated embodiment FIG. 2a, the cylindrical surface of the rotor 22 is covered by a microporous membrane 46. The microporous membrane preferably has a pore size less than about 1 micron, and sufficiently small to block passage of cellular blood components, such as, red cells, white cells and platelets, through the membrane, while allowing the passage through the membrane of plasma that includes molecular waste products of metabolism. As pointed out earlier, the cellular blood components that do not pass through the membrane are discharged through the outlet port 36 and into a return flow path 38 for return to the patient.

The plasma comprising, inter alia, metabolic waste molecules and water that passes through the membrane is referred to herein as "filtered plasma." The molecular waste products of metabolism may be described as including medium or middleweight molecules and small or small weight molecules. While the size ranges of these molecules is difficult to define with precision, middleweight molecules are understood to fall generally in the range of about 500 to 60,000 Daltons. Similarly small molecules are understood to fall broadly in the range of less than about 500 Daltons.

It is contemplated that microporous membrane 46 may also have a pore size that also allows large molecules to pass therethrough. Large molecules, such as molecules larger than middleweight molecules, may not be characterized as the by-products of metabolism, which are to be removed, but may be needed by the patient for certain physiological functions. Accordingly, the illustrated embodiment contemplates that it may be desirable to return to the patient large molecules in general or a range of large molecules, although that may not be required.

The filtered plasma comprising the waste that passes through the membrane 46 is collected through a collection sink, such as an array of passageways 48 within the rotor, which channel the filtered plasma to an internal axial passage 49 to outlet 50 for removal through outlet flow path 52, and for conveyance to the second stage of the system. In an apparatus where the second stage is integrated into the same structure as the first stage, the filtered plasma could, of course, be conveyed directly to the second stage and would not necessarily be withdrawn from the apparatus.

Turning more specifically to the process employed in the first stage, with the exemplary apparatus depicted in FIG. 2a, the removal of blood cells from the whole blood of a patient is herein referred to as hemofiltration, and microporous membrane 46 may be referred to as a hemofiltration membrane. More specifically, the membrane is preferably a biocompatible synthetic material such as polysulfone, polyacrylonitrile, polyvinyl-alcohol, polyamide, polycarbonate, or other suitable material. As pointed out earlier, the average or effective pore size of the microporous membrane 46 preferably sufficiently small to prevent the passage of blood components therethrough, while allowing plasma carrying the by-products of metabolism to pass through the membrane. More particularly, the membrane 46 may preferably allow passage of molecules up to about 60,000 Daltons but desirably not have a pore size greater than about 1 micron to avoid the passage of red cells, white cells and platelets while allowing plasma including large, medium and small molecules and water to pass through the membrane.

FIG. 2b illustrates an alternative embodiment of a hemofiltration apparatus for employment in the first stage of the blood processing system and method shown in FIG. 1. In FIG. 2b, the microporous hemofiltration membrane 46 is mounted on the inside surface of the stationary housing chamber 21 instead of on the surface of the rotor 22. More specifically, the membrane 46 is carried by the inside cylindrical surface 32 of the housing, and overlies an array of passageways, generally at 56 (not shown in detail) for collecting filtered plasma passing through the membrane.

More specifically, as with FIG. 2b, the rotor 22 has an outside diameter smaller than the inside diameter of the cylindrical housing 20, forming a gap 28 between the outer surface of the rotor and the inside surface of the housing, which mounts the hemofiltration membrane 46. Blood is received from the patient through inlet flow path 14 and inlet port 34, passing into the gap 28 formed between the outside of the surface of the rotor and the inside surface of the housing. Plasma, with large, medium and small molecules and water is allowed to pass through the microporous membrane, while cellular components of blood such as red cells, white cells and platelets, are not allowed to pass through the membrane and flow through the gap to the outlet port 36 where they are removed and conveyed, via return flow path 38, to the patient. In this embodiment, the rotor 22 is rotatably mounted between a pair of pivot bearings 24 and 26, and does not necessarily employ the array of passageways 48 as described in connection with FIG. 2a, although a hemofiltration membrane could also be located on the rotor as described above (in addition to the membrane on the surface of the housing chamber) to provide additional filtration capacity that could further speed the processing of blood.

In the illustrated embodiment of FIG. 2b, the surface of the rotor is solid and impermeable. Plasma passing through the membrane 46 is collected by an array of passageways 56 formed in the facing inside surface 32 of housing chamber 21, which collect and convey the plasma, together with large, medium and small molecules and water to outlet 54 from the housing.

Figure 3A:
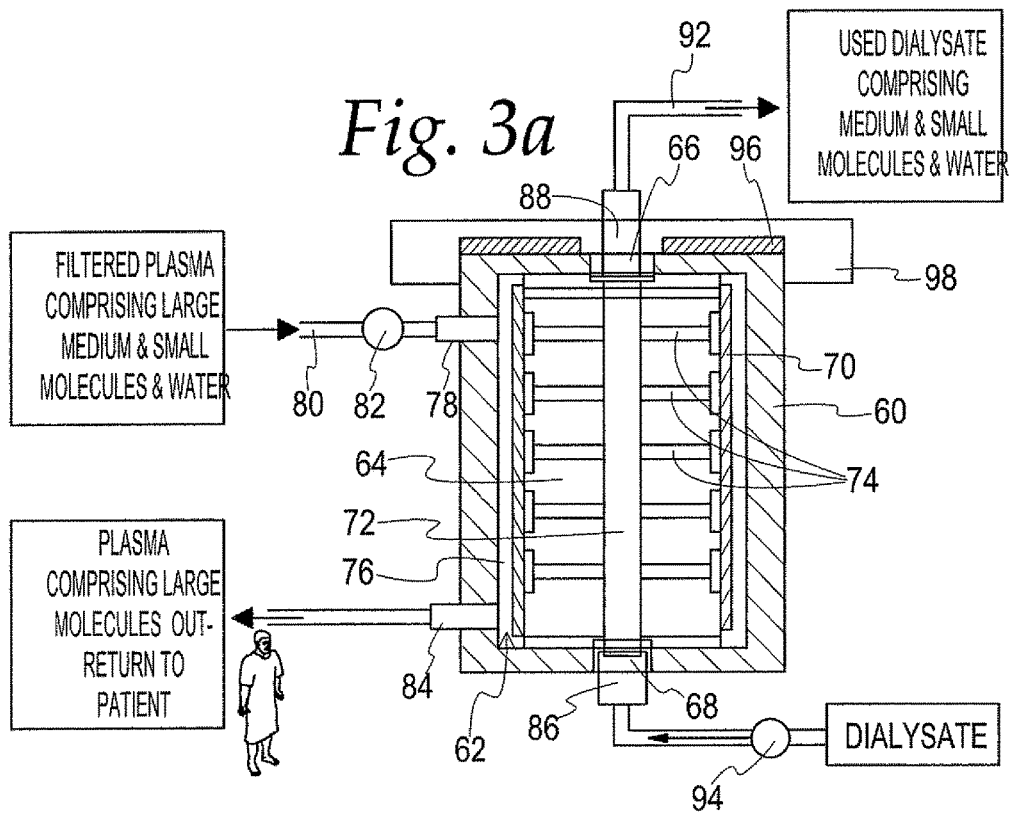
FIG. 3a is a side cross-sectional view of one embodiment of a blood processing apparatus that the system and method shown in FIG. 1 can incorporate for performing hemodialysis.
Figure 3B:
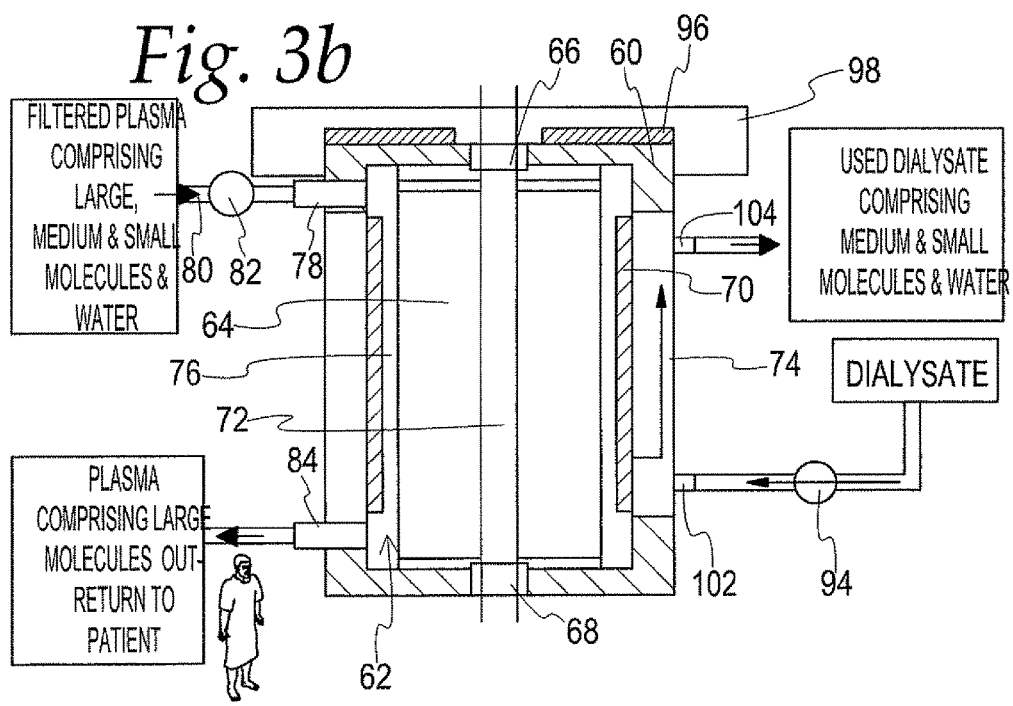
FIG. 3b is a side cross-sectional view of another embodiment of a blood processing apparatus that the system and method shown in FIG. 1 can incorporate for the purpose of performing hemodialysis.

Whether the embodiment of FIG. 2a, 2b or other is used in the first stage of the process, the filtered plasma, preferably including large, medium and small molecules and water, is conveyed to the second stage of the system, which may employ, for purposes of this description, an apparatus as shown in FIGS. 3a and/or 3b for processing the plasma to remove molecules of selected size such as medium and small molecules plus excess water. More specifically, the exemplary devices shown in FIGS. 3a and 3b, as described in more detail below, preferably function by processing the filtered plasma into contact with a diffusion membrane. As shown in FIGS. 3a and 3b, the diffusion membrane comprises a hemodialysis membrane, and the filtered plasma contacts one side of the hemodialysis membrane while the other side of the membrane is preferably simultaneously contacted with fresh dialysis solution. Thus, a concentration gradient is created which induces the passage of the medium and small molecules and water from the plasma.

Turning specifically to FIG. 3a, the dialysis apparatus shown there employs a housing 60 defining a generally cylindrical internal chamber 62. A generally cylindrical spinner or rotor 64 is rotatably mounted within the housing chamber 62 between pivot bearings 66 and 68. A diffusion membrane 70 is mounted on the surface of the rotor 64, for rotation with the rotor. The rotor includes an elongated central passageway 72 connected to an array of passageways 74 that communicate between the central passageway and the outermost surface of the rotor to collect fluid passing through the diffusion membrane 70. Similar to FIG. 2a, the outer diameter of the rotor (including the membrane carried by the rotor) is smaller than the inside diameter of the cylindrical housing chamber 62 so as to define a gap 76 between the outer surface of the rotor and the inner surface of the chamber 62.

For receiving filtered plasma from the first stage of the process, the housing 60 includes an inlet port 78, which is shown communicating with an inlet flow line 80, via pump control 82. The inlet port 78 communicates with the gap 76 between the rotor and inside surface of the housing, so as to direct filtered plasma through the gap to an outlet port 84 located at the opposite end of the housing.

As illustrated in FIGS. 3a and 3b, the pivot bearings 66 and 68 have fluid passageways therethrough, forming a fluid inlet 86 for fresh dialysis solution at one end and a dialysate fluid outlet 88 at the opposed end of the housing. This arrangement allows fresh dialysis solution to flow from a source, such as a bag or other container or source, through an inlet passageway 86 and through pivot bearing 68 into the central passageway 72 of the rotor. From the central passageway, the dialysis solution flows through the passageway array 74 into contact with the inside or underside surface of the diffusion membrane 70, such as a hemodialysis membrane, that faces the rotor surface. Dialysis solution containing waste, such as medium and small molecule metabolism by-products (i.e. dialysate) is removed from the housing through the outlet port 88 in the opposed pivot bearing, and from there through an outlet passageway 92 for disposal or further processing. The flow rate of dialysis solution through the rotor may be controlled by a suitable control system, for example, a computer control system that may be operator or software controlled to regulate the flow rate of the dialysate through the rotor via pump 94.

In a preferred embodiment, the diffusion membrane may be comprised of any suitable material with diffusion characteristics that allow water and small and medium size molecules to pass from the filtered plasma therethrough, and into the dialysis solution for removing substantial amounts of the medium and small molecule metabolism by-products, together with excess water. More specifically, the diffusion membrane 70 may comprise a medium to high flux membrane, for example of polysulfone, cellulose, triacetate or acrylonitrile material. The membrane preferably is suited, as mentioned above, for removal of water and small and medium size molecules, (such as molecules having a size less than about 60,000 Daltons), allowing large molecules or selected ranges of large molecules to remain in the filtered plasma.

The rotor in the dialysis device shown in FIG. 3a is rotated relative to the housing, in substantially the same manner as described in connection with FIG. 2a, such as by the employment of a magnetic ring 96 on the rotor which is driven indirectly by a rotating magnetic field generated by a drive unit 98 associated with a reusable system or hardware device into which the dialysis unit is mounted or associated. By way of a magnetic drive system, the rotor may be rotated at sufficient speed such that turbulence is generated in the filtered plasma flowing through the gap 76 that will encourage high transport rates of water, medium and small molecules through the membrane and into the dialysis solution. More specifically, the size of the gap and the flow rate of the filtered plasma and rotational speed of the rotor may be chosen so as to create shear forces in the fluid, such as by Couette flow, between the relatively moving surfaces. More specifically, the rotational speed of the rotor relative to a stationary housing wall and the gap size may be selected so as to create a series of Taylor vortices within the gap. Such vortices may serve to create sufficiently high shear rates along the surface of the diffusion membrane facing the gap so as to continuously effectively sweep the surface of the membrane that faces the gap, reducing potential clogging or deterioration of the performance of the diffusion membrane. Details of such a system are described in one or more of the patents and applications identified earlier and incorporated by reference and Taylor-vortex enhanced separation is a known phenomena and process for filtering fluids and performing dialysis. It should be noted that the two stage system described here does not require that both stages employ such high fluid shear, Couette flow or Taylor vortices, although it is contemplated that the use of such would potentially enhance performance.

When used in the two stage process and system shown in FIG. 1, the dialysis device of FIG. 3a is operated by flowing filtered plasma, comprising large, medium and small molecules and water from the first stage, through inlet port 80 into the gap 76 between the rotor and housing. More specifically the filtered plasma passes between the surface of the diffusion membrane 70 facing the gap, and the inside surface of the cylindrical internal chamber 62 of housing 60. The filtered plasma flows along the gap to the outlet port 84, which is located at the opposite end of the elongated housing 60, with water, medium and small size molecules being removed through the diffusion membrane as the plasma proceeds along the gap between the ends of the rotor.

Simultaneously with the flow of filtered plasma through the gap 76, standard fresh dialysis solution may be directed into the passageways 72, 74 within the rotor through dialysis solution inlet 86. This fresh dialysis solution is directed through the array of passageways 74 in the rotor into contact with the surface of the diffusion membrane facing the rotor. In accordance with known principles, the dialysis solution creates a concentration gradient across the membrane, inducing transport through the membrane. Specifically, the concentration gradient induces the transport or passage of both waste molecules and water through the membrane. As noted earlier, in accordance with one aspect of the present invention, it is contemplated that medium and small size molecules, which generally comprise much of the molecular waste byproduct of metabolism, will be drawn through the diffusion membrane into the dialysis solution, while larger molecules, which are often needed for physiological processes in the patient, are retained with the plasma. The depleted or used dialysis solution, i.e., dialysate, flows from the array of passageways 74 in the rotor to dialysate outlet 88 at the opposite end of the rotor. From there, the used dialysate, which now includes medium and small molecules from the filtered plasma, as well as water removed from the plasma, is withdrawn from the rotor and conveyed to any suitable facility for disposal, storage or further processing to reclaim the dialysate if desired.

As may be seen in FIG. 3a, the dialysis solution and the filtered plasma flow in generally opposite directions through the dialysis device. As a consequence, a relatively large diffusion gradient is maintained between the plasma and the dialysis solution along the flow paths. In other words, plasma that has already been subjected to processing through the gap is exposed to fresh dialysis solution, providing a relatively large concentration gradient across the diffusion membrane for the removal of molecules and water.

Closer to the dialysis solution exit and the filtered plasma inlet, where the dialysis solution now contains some medium and small molecules and water removed from filtered plasma, the plasma that is being processed on the opposite side of the diffusion membrane has larger concentrations of those molecules and water thus maintaining a relatively high concentration gradient across the membrane to induce passage of the desired molecules and water across the membrane from the filtered plasma into the dialysis solution.

Because the cellular components within the plasma, i.e. red cells, white cells and platelets have been substantially removed during processing through the first stage, the filtered plasma that is introduced into the second stage and, for example, into the dialysis apparatus shown in FIG. 3a, is substantially reduced of those cellular components. As a consequence, the transport process, such as by diffusion, across the diffusion membrane is believed to be faster and more efficient because there is less potential for blood cells coming into contact with the surface of the diffusion membrane, blocking diffusion across the membrane or otherwise interfering or reducing the efficiency of the diffusion process across the diffusion membrane. This is understood to allow a faster flow rate of filtered plasma through the second stage and through the device shown in FIG. 3a, substantially reducing the time for dialysis as compared to the time that would be required if the filtered plasma contained the quantities of blood cells typically contained in the whole blood of the patient.

FIG. 3b illustrates an alternative apparatus that may be employed in the second stage of the processing system illustrated in FIG. 1. FIG. 3b is similar to the apparatus shown in FIG. 3a, except that diffusion membrane 70 is located on the inside surface of the housing chamber 62. In this embodiment, the outer surface of the rotor is preferably a smooth continuous surface. Because dialysis solution does not flow through the rotor in this example, there is no inlet and outlet port for dialysis solution through the pivot bearings 66 and 68, simplifying construction. In the embodiment shown in FIG. 3b, the surface of the housing internal chamber 62 employs an array of passageways formed in it to bring dialysis solution in contact with the outermost surface of the diffusion membrane, such as a hemodialysis membrane (the surface facing the inside surface of the chamber 62).

In the embodiment shown in FIG. 3b, filtered plasma comprising large, medium and small molecules and water from the first processing stage is conveyed through inlet port 78 into the gap 76 between the outer surface of the rotor 64 and the surface of the diffusion membrane 70 facing the rotor. The filtered plasma proceeds through the gap, from the inlet 78 to the spaced apart outlet port 84. Simultaneously, dialysis solution is brought into contact with the outer surface of the diffusion membrane, which faces and is in contact with the inside surface of the housing internal chamber 62. More specifically, the housing includes an inlet port 102 for fresh dialysis solution that communicates with the array of passageways (not shown in detail) that face the outer surface of the diffusion membrane and a dialysate outlet port 104 for removal of used or spent dialysate, including medium and small molecules and water removed from the plasma as it is processed through the apparatus. In a manner similar to that described in FIG. 3a, fresh dialysis solution is introduced into the device at approximately the same axial location where filtered plasma (that has been processed through the device) is removed, and used or spent dialysate is removed from the apparatus through the outlet port at approximately the same axial location at which the inlet port introduces filter plasma into the system. This reverse flow arrangement tends to maximize the concentration gradient along the processing surface of the diffusion membrane to enhance the removal of the molecules and water from the filtered plasma.

The rotor 64 in the apparatus shown in FIG. 3b may be rotated by a suitable drive system such as described in FIGS. 2a, 2b and 3a. Preferably the rotor is rotated at a speed such that turbulence is induced in the gap 76, creating shear forces along the gap surfaces such as by Couette flow, and more specifically, Taylor vortices as described above, to assist in reducing clogging, blocking or interfering with the diffusion membrane, and thereby enhancing the filtration rate.

Figure 4:
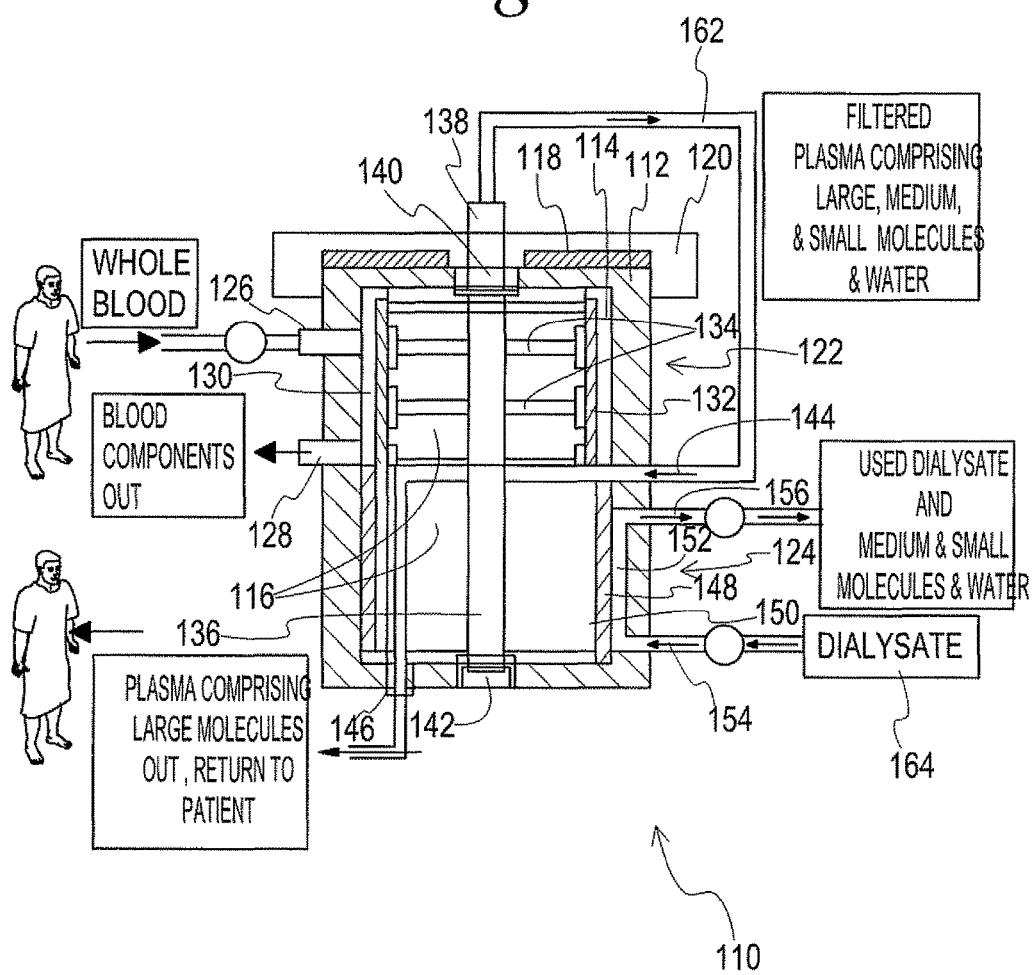
FIG. 4 is a side cross-sectional view of one embodiment of a single blood processing apparatus that the system and method shown in FIG. 1 can incorporate for the purpose of separating cellular components of blood from plasma including metabolic waste and for performing hemodialysis.

FIGS. 2 and 3 are exemplary of apparatus for use in a two stage process in which each stage is carried out in separate apparatus. However, in keeping with the broader aspects of the present disclosure, the different processing stage may be carried out in the same apparatus if desired. An example of such an alternative is illustrated in FIG. 4. As shown there, the processing apparatus, generally at 110 includes an elongated outer cylindrical housing 112 with a cylindrical internal chamber 114. An elongated cylindrical spinner or rotor 116 is rotably mounted within the chamber and driven by a suitable drive system, such as the system described earlier, with a magnetic ring 118 carried by the rotor and an external magnetic field drive unit 120 associated with the hardware or other device with which the processing apparatus 110 is cooperatively associated.

As illustrated in FIG. 4, the multi-stage processing occurs within the same apparatus by employing separate zones for different processing stages. Specifically, the apparatus of FIG. 4 includes a hemofiltration zone 122 in which cellular blood components are removed from whole blood of the patient, and a hemodialysis zone 124 in which filtered plasma, comprising large, medium and small molecules in water, is processed for the removal of medium and small molecules and water, leaving plasma comprising large molecules for return to the patient.

More specifically, the housing 112 includes a whole blood inlet 126 and a spaced apart blood component outlet 128 located within the hemofiltration zone 122. The portion of the rotor 116 located within the hemofiltration zone is sized such that the outer diameter of the rotor is smaller than the inside diameter of the housing so as to provide a gap 130 between the rotor and the housing surfaces. The outside surface of the rotor within the hemofiltration zone mounts a hemofiltration membrane 132 which rotates with the rotor. Within the hemofiltration zone, the rotor has an array of passageways 134 that communicate from the inside surface of the hemofiltration membrane to a central passageway 136 for conveying filtered plasma comprising large, medium and small molecules and water from the rotor through an outlet 138 in pivot bearing 140. It is noted that in this embodiment, the opposed pivot bearing 142 does not require an inlet or outlet passageway therethrough.

In the hemodialysis zone 124, the housing includes a filtered plasma inlet 144 at one end of the hemodialysis zone and a filtered plasma outlet 146 at the other axial end of the dialysis zone. In the hemodialysis zone, a diffusion membrane, such as a hemodialysis membrane, 148 is located in a stationary position around the inside surface of the housing 112, facing a gap 150 formed between the outside surface of the rotor and the inside surface of the housing, i.e. the facing surface of the diffusion membrane mounted on the housing.

The housing in the hemodialysis zone includes an array of passageways formed on the inside surface for communicating with the side of the diffusion membrane facing away from the gap. More specifically, the housing includes such an array of passageways 152 formed on the inside surface of the housing and communicating between a fresh dialysis solution inlet 154 and a dialysate outlet 156.

In this system, as with the devices described above, the rotor may be rotated by a suitable magnetic ring 118 attached to the rotor, which is rotated by a magnetic drive unit associated with the hardware or durable system component with which the apparatus of 110 is cooperatively associated. As with the prior disclosed devices, it is desirable for the rotor to be rotated at a speed such that blood flowing through the gap 130 in the hemofiltration zone and filtered plasma flowing through gap 150 in the hemodialysis zone experience substantial turbulence and shear forces, such as by Couette flow or Taylor vortices, to reduce the potential for clogging or interference with the hemofiltration and diffusion membranes and enhance the speed and efficiency of the processing through the apparatus. More specifically, the rotational speeds may be such as to generate Taylor vortices within the gaps 130 and 150, as illustrated in FIGS. 5 and 6. Taylor vortices have been found in other applications to create relatively high shear forces along the surfaces of the membranes, causing, in effect, a sweeping action that tends to remove particulate from the surface of the membrane, maintaining the membrane surface available for hemofiltration and/or hemodialysis.

Turning now to the process employed in the apparatus illustrated in FIG. 4, which employs a two stage process. Whole blood is conveyed from the patient, through an inlet line, via optional pump control, into whole blood inlet port 126 and into the gap 130 between the inside surface of the housing 112 and the facing surface of the hemofiltration membrane 132, located in the hemofiltration zone 122. Whole blood flows axially along the gap to the blood component outlet 128, where which a portion of the blood, including the blood all components, e.g. red cells, white cells and platelets, is removed from the hemofiltration zone for return to the patient.

The hemofiltration filter membrane is preferably a microporous filter, substantially as described earlier with respect to FIGS. 2a and 2b, having a pore size that allows plasma comprising large, medium and small molecules and water to pass through the membrane and into an array of passageways 134 adjoining the inside surface of the membrane for channeling the filtered plasma to a central passageway 136 extending axially along the rotor and to outlet 138.

The filtered plasma, including large, medium and small molecules and water, are directed, via return flow path 162, into the filtered plasma inlet 144 in the hemodialysis zone of the housing. From the filtered plasma inlet 144, the filtered plasma is conveyed into the gap 150 between the outer surface of the rotor 116 and the facing surface of diffusion membrane 148. The filtered plasma proceeds axially through the gap 150 to outlet port 146, from which the treated plasma is removed. At this outlet port 146, the treated plasma has been subjected to dialysis and comprises principally plasma plus large molecules for return to the patient, and is depleted of medium and small molecules and water.

The filtered plasma has been subjected to dialysis preferably by passing fresh dialysis solution from a source 164 into dialysis solution 154 inlet and into the array of passageways 152 which bring the solution into contact with the outside surface of the diffusion membrane 148 (the surface of the diffusion membrane which faces the inside surface of the housing). The dialysis solution creates a concentration gradient across the diffusion membrane 148, causing the passage of medium and small molecules and water across the membrane and into the dialysis solution, which is removed through dialysate outlet 156 for disposal or further processing. As with FIG. 3b, the dialysis solution flows between the inlet 154 and outlet 156, in the opposite direction that the filtered plasma flows between the filtered plasma inlet 144 and outlet 146, so as to maintain a substantial concentration gradient across the diffusion membrane between the filtered plasma and the dialysis solution.

Therefore, the processing apparatus 110 of FIG. 4 allows two stage processing to be employed in the same housing, utilizing a single housing and single rotor which is subdivided into separate hemofiltration and hemodialysis zones by suitable partitions or seals, and potentially reduces the size and complexity of the reusable or durable apparatus that may be employed with the processing apparatus 110. Such a system has the further advantage that only a single magnetic drive system may be required, and a single attachment point be required for the single processing apparatus.

Although described in connection with the preferred and illustrated embodiments, the subject matter is not limited to these embodiments, may be modified in such manner that would be apparent to those skilled in the field, and reference is required to the appended claims for the full scope of the subject matter disclosed herein.

The invention claimed is:

1. A blood processing system for performing hemodialysis on a patient to remove metabolic waste from the patient's blood comprising:
    a blood processing apparatus having a first stage device and a second stage device downstream from the first stage device,
    a first flow path for fluid communication from the patient to said first stage device of the blood processing apparatus,
    said first stage device of the blood processing apparatus comprising:
        spaced apart first inner and first outer surfaces defining a first gap therebetween, the flow path communicating with the first gap for flowing blood therethrough;
        at least one of the first inner and first outer surfaces carrying a filter membrane,
        a first drive assembly for causing relative movement between the first inner and first outer surfaces to create movement of the blood within the first gap that induces transport of plasma comprising waste through the membrane while substantially preventing the passage of blood cells therethrough to provide filtered plasma comprising waste that is substantially reduced of blood cells,
    said second stage device of the blood processing apparatus comprising:
        a second inner surface and a second outer surface spaced apart to define a second gap,
        at least one of the second inner and second outer surfaces carrying a diffusion membrane having a facing side and an opposite side,
        a passageway in communication with the opposite side of the diffusion membrane for conveying a solution along the opposite side of the diffusion membrane;
        a second drive assembly causing relative movement between the second inner and outer surfaces to create movement of plasma comprising waste within the second gap that induces transport of waste comprising small molecules and medium molecules by diffusion from the facing side of the diffusion membrane to the solution conveyed along the opposite side of the diffusion membrane while the passage of said plasma comprising large molecules from the facing side of the diffusion membrane to the opposite side of the diffusion membrane is substantially prevented, and a second flow path for fluidly communicating the plasma comprising large molecules from the facing side of the diffusion membrane back to the patient.

2. The blood processing system of claim 1 further comprising an access device for withdrawing and returning blood, blood cells and plasma to and from a patient.

3. The blood processing system of claim 1 further comprising a source of anti-coagulant in communication with said flow path between the patient and said blood processing apparatus.

4. The blood processing system of claim 1 further comprising a third flow path for fluid communication between said blood processing apparatus and said patient for conveying blood cells from said first stage device for return to the patient.

5. The blood processing system of claim 4 further comprising a fourth flow path for fluid communication with said blood processing apparatus for conveying waste from said apparatus.

6. The blood processing system of claim 1 wherein said filter membrane comprises at least one of a microporous membrane and a fibrous membrane.

7. The blood processing system of claim 6 wherein said filter membrane has a pore size sufficiently small to prevent the passage of red blood cells, platelets and white blood cells.

8. The blood processing system of claim 1 wherein said diffusion membrane blocks the passage of molecules having a molecular weight substantially greater than about 60,000 Daltons.

9. The blood processing system of claim 1 wherein said first and/or second drive assembly causes relative movement between the first inner and first outer surfaces and/or between the second inner and second outer surfaces at a selected surface velocity to create at least one of Couette flow and Taylor vortices therebetween.

* * * * *